(12) United States Patent
Wang et al.

(10) Patent No.: US 12,011,245 B2
(45) Date of Patent: Jun. 18, 2024

(54) SURGICAL ROBOT MECHANISM WITH SINGLE-PORT AND MULTI-PORT MINIMALLY INVASIVE SURGERY FUNCTIONS

(71) Applicant: TIANJIN UNIVERSITY, Tianjin (CN)

(72) Inventors: Shuxin Wang, Tianjin (CN); Zhenxuan Hu, Tianjin (CN); Guokai Zhang, Tianjin (CN); Dezhong Gao, Tianjin (CN); Jianmin Li, Tianjin (CN); Jinhua Li, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 931 days.

(21) Appl. No.: 16/981,094

(22) PCT Filed: Oct. 25, 2018

(86) PCT No.: PCT/CN2018/111897
§ 371 (c)(1),
(2) Date: Sep. 15, 2020

(87) PCT Pub. No.: WO2020/082299
PCT Pub. Date: Apr. 30, 2020

(65) Prior Publication Data
US 2021/0251708 A1 Aug. 19, 2021

(51) Int. Cl.
*A61B 34/30* (2016.01)
*A61B 17/00* (2006.01)
(Continued)

(52) U.S. Cl.
CPC ........ *A61B 34/70* (2016.02); *A61B 17/00234* (2013.01); *A61B 34/37* (2016.02); *A61B 90/50* (2016.02); *B25J 18/00* (2013.01)

(58) Field of Classification Search
CPC ......... A61B 34/00; A61B 34/37; A61B 34/30; A61B 34/70; A61B 19/21; A61B 19/203;
(Continued)

(56) References Cited

U.S. PATENT DOCUMENTS

2010/0274087 A1* 10/2010 Diolaiti ............. A61B 1/00087
700/275
2017/0000572 A1 1/2017 Moctezuma de la Barrera et al.

FOREIGN PATENT DOCUMENTS

CN 106037937 10/2016
CN 106361440 2/2017
(Continued)

OTHER PUBLICATIONS

International Search Report and Written Opinion issued in PCT/CN2018/111897, dated Jul. 29, 2019.
(Continued)

*Primary Examiner* — Vi X Nguyen
(74) *Attorney, Agent, or Firm* — Pillsbury Winthrop Shaw Pittman, LLP

(57) ABSTRACT

A surgical robot mechanism with single-port and multi-port minimally invasive surgery functions includes: a bracket; and a manipulator connected to the bracket, and supported by the bracket, the manipulator includes: a support arm movable along the bracket; a function conversion frame fixed on the support arm and configured for the surgical robot mechanism to switch between a single-port minimally invasive surgery mode and a multi-port minimally invasive surgery mode; a plurality of posture adjustment arm assemblies connected to the function conversion frame, each posture adjustment arm assembly configured to adjust a position and posture of a surgical tool connected thereto for performing a surgical operation.

5 Claims, 4 Drawing Sheets

(51) Int. Cl.
  *A61B 34/00*    (2016.01)
  *A61B 34/37*    (2016.01)
  *A61B 90/50*    (2016.01)
  *B25J 18/00*    (2006.01)

(58) Field of Classification Search
  CPC ............... A61B 19/5244; A61B 90/50; A61B 17/00234; A61B 19/201
  See application file for complete search history.

(56) References Cited

FOREIGN PATENT DOCUMENTS

| CN | 106691591  | 5/2017 |
|----|------------|--------|
| CN | 206836961  | 1/2018 |
| CN | 108433811  | 8/2018 |
| EP | 2578177    | 4/2013 |
| WO | 2018059039 | 4/2018 |

OTHER PUBLICATIONS

Extended European Search Report issued in corresponding European Patent Application No. 18938213.8, dated Sep. 9, 2021.

\* cited by examiner

SURGICAL ROBOT MECHANISM WITH SINGLE-PORT AND MULTI-PORT MINIMALLY INVASIVE SURGERY FUNCTIONS

This application is a national stage application of PCT patent application no. PCT/CN2018/111897, filed on Oct. 25, 2018.

TECHNICAL FIELD

The present disclosure relates to the field of minimally invasive surgical robots, in particular to a surgical robot mechanism with single-port and multi-port minimally invasive surgery functions.

BACKGROUND

Minimally invasive surgery has many advantages such as a small wound, less bleeding, fast recovery time and good cosmetic effect. Traditional minimally invasive surgery tools are mostly long and straight rod-shaped, which are held by a doctor and inserted through a small wound in a chest, an abdomen or other parts, and a surgical operation would be completed under the assistance of an endoscope image on a monitor screen, cooperating with a medical endoscope. In such an operation mode, a surgeon, an endoscope-holding doctor, and other assistant doctors are required to cooperate with each other to perform the surgical operation. During the surgical operation, a problem such as surgical tool interference usually occurs for multiple reasons, such as uncoordinated cooperation, or unreasonable visual field in the monitor screen, and the movement of surgical instruments not conforming to intuitive operation rules, which affects smooth progress of the operation.

A minimally invasive surgical robot is a surgical robot developed for minimally invasive surgery. The working principle of the surgical instruments thereof is similar to that of traditional minimally invasive surgical instruments. The long and straight rod-shaped surgical instrument is inserted into the patient's body cavity through the small wound. The doctor does not directly operate a robotic surgical instrument, but controls movements of the surgical instruments through an operating platform of the robot. A minimally invasive surgical robot mostly employs a master-slave control system, and according to principles such as kinematics, dynamics, control system principles, robotics, machine vision, etc., movements of surgical instruments are enabled to accurately map hand movements of the doctor, so as to achieve a more efficient and safer operation.

A minimally invasive surgical robot can be roughly divided into three types: a multi-port minimally invasive surgical robot, a single-port minimally invasive surgical robot and a natural orifice minimally invasive surgical robot. Based on characteristics and constraints of different types of surgery, each of these three types of surgical robots performs a surgery according to the adapted environment. Therefore, a certain type of surgical robot can only be applied to one type of surgery, that is, the multi-port minimally invasive surgical robot can only be used for multi-port minimally invasive surgery, the single-port minimally invasive surgical robot can only be used for single-port minimally invasive surgery, and the natural orifice surgical robot can only be used for natural orifice surgery.

In view of a wide variety of minimally invasive surgeries, different lesion locations, different environmental requirements, and complicated internal manipulation space constraints, a certain type of minimally invasive surgical robot cannot fully adapt to the surgical field it is aimed at. A hospital needs to be equipped with multiple types of surgical robots to meet surgical needs of different patients.

SUMMARY

The present disclosure provides a surgical robot mechanism with single-port and multi-port minimally invasive surgery functions, comprising: a bracket; and a slave manipulator connected to the bracket, and supported by the bracket, the slave manipulator comprising: a support arm movable along the bracket; a function conversion frame fixed on the support arm and operated for the surgical robot mechanism to switch between a single-port minimally invasive surgery mode and a multi-port minimally invasive surgery mode; a plurality of posture adjustment arm assemblies connected to the function conversion frame and operated to adjust positions and postures of surgical tools; and a plurality of surgical tools connected to the plurality of posture adjustment arm assemblies respectively and operated to perform a surgical operation.

As can be seen from above technical solutions, an embodiment of the present disclosure has at least the following beneficial effects:

A function conversion frame is provided, and by adjusting the function conversion frame, the surgical robot mechanism can switch between a single-port minimally invasive surgery function and a multi-port minimally invasive surgery function. A posture adjustment arm assembly structure enables surgical tools, carried by an end, multi-degree-of-freedom movement in space, so that it is easy to be adjusted according to specific lesion environment. The present disclosure has both single-port minimally invasive surgery and multi-port minimally invasive surgery functions, and an applicable environment thereof can be flexibly changed by reorganizing the structure of the robot and selecting the surgical tools to be carried.

BRIEF DESCRIPTION OF THE ACCOMPANYING DRAWINGS

The accompanying drawings are used to provide a further understanding of the present disclosure and constitute a part of the specification, and together with the following detailed descriptions, the accompanying drawings are used to explain the present disclosure, but do not constitute a limitation to the present disclosure, in which.

SYMBOL DESCRIPTION

Figure 1:
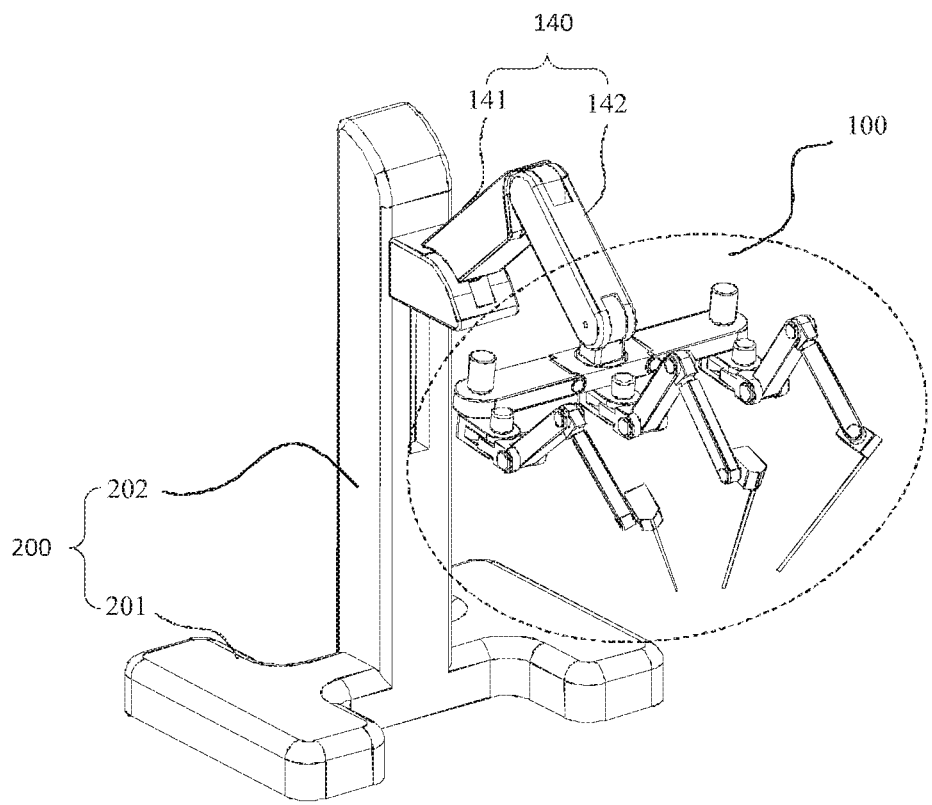
FIG. 1 is a schematic diagram of an overall structure of a surgical robot mechanism with single-port and multi-port minimally invasive surgery functions according to an embodiment of the disclosure.

100—slave manipulator;
110—function conversion frame;
111—base;
112—first cantilever;
113—second cantilever;
120—posture adjustment arm assembly;
121—first active arm;
122—active arm joint;
123—second active arm;
124—passive arm joint;
125—passive arm;
130—surgical tool;
140—support arm;
141—first arm;
142—second arm;
200—bracket;
201—I-shaped base;
202—support pillar;
R1, R2, R3, R4, R5, R6, R7, R8—first axis, second axis, third axis, fourth axis, fifth axis, sixth axis, seventh axis, and eighth axis.

DETAILED DESCRIPTION

The present disclosure provides a surgical robot mechanism with single-port and multiple-port minimally invasive surgery functions. It has both single-port minimally invasive surgery and multi-port minimally invasive surgery functions, and an applicable environment thereof can be flexibly changed by reorganizing the structure of the robot and selecting the surgical tool(s) to be carried.

In order to make an objective, a technical solution, and an advantage of the present disclosure clearer, the present disclosure will be described further in detail with reference to specific embodiments and accompanying drawings.

An embodiment of the present disclosure provides a surgical robot mechanism with single-port and multi-port minimally invasive surgery functions. As illustrated in FIGS. 1 to 4, the surgical robot mechanism comprises: a bracket 200 and a slave manipulator 100. The slave manipulator 100 is connected to the bracket 200, and the slave manipulator 100 is supported by the bracket 200 and moves up and down along the bracket 200.

The bracket 200 comprises an I-shaped base 201 and a support pillar 202, and the support pillar 202 is fixed on the I-shaped base 201.

The slave manipulator 100 comprises a support arm 140, a function conversion frame 110, a posture adjustment arm assembly 120 and a surgical tool 130.

The support arm 140 includes a first arm 141 and a second arm 142. The first arm 141 is fixed on the support pillar 202, and the second arm 142 is rotatably connected to the first arm 141.

The function conversion frame 110 is rotatably connected to the second arm 142 of the support arm 140, and is operated for switching between a single-port minimally invasive surgery function and a multi-port minimally invasive surgery function of the surgical robot mechanism.

Figure 2:
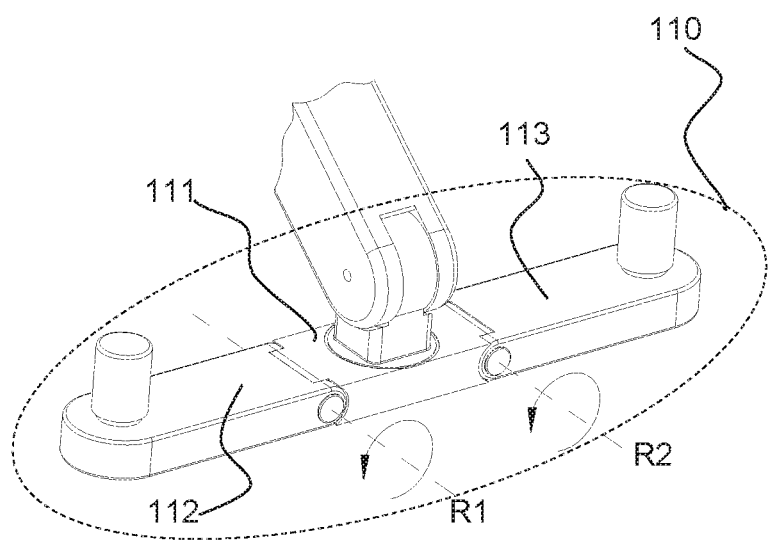
FIG. 2 is a schematic structural diagram of a function conversion frame of a surgical robot mechanism with single-port and multi-port minimally invasive surgery functions according to an embodiment of the disclosure.

The function conversion frame 110 is specifically illustrated in FIG. 2, comprising a base 111, a first cantilever 112 and a second cantilever 113. The base 111 is rotatably connected to the second arm 142 of the support arm 140, and one end of the base 111 is connected to the first cantilever 112 by a passive revolute pair, and the other end of the base 111 is connected to the second cantilever 113 by a passive revolute pair. The first cantilever 112 and the second cantilever 113 are respectively rotatable relative to the base 111 about a first axis R1 and a second axis R2.

Figure 3:
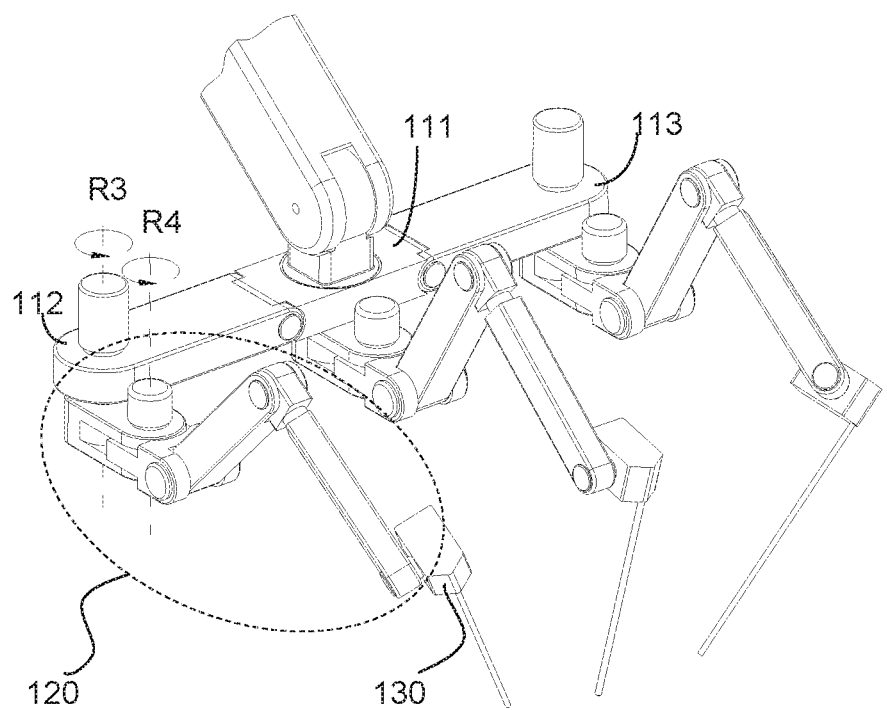
FIG. 3 is a schematic structural diagram of a multi-port minimally invasive surgery mode of a surgical robot mechanism with single-port and multi-port minimally invasive surgery functions according to an embodiment of the disclosure.

A plurality of posture adjustment arm assemblies 120 are connected to the function conversion frame 110, and operated to adjust positions and postures of surgical tools 130. FIGS. 1 and 3 comprise three posture adjustment arm assemblies 120, which are fixed to the base 111, the first cantilever 112 and the second cantilever 113, respectively.

Figure 4:
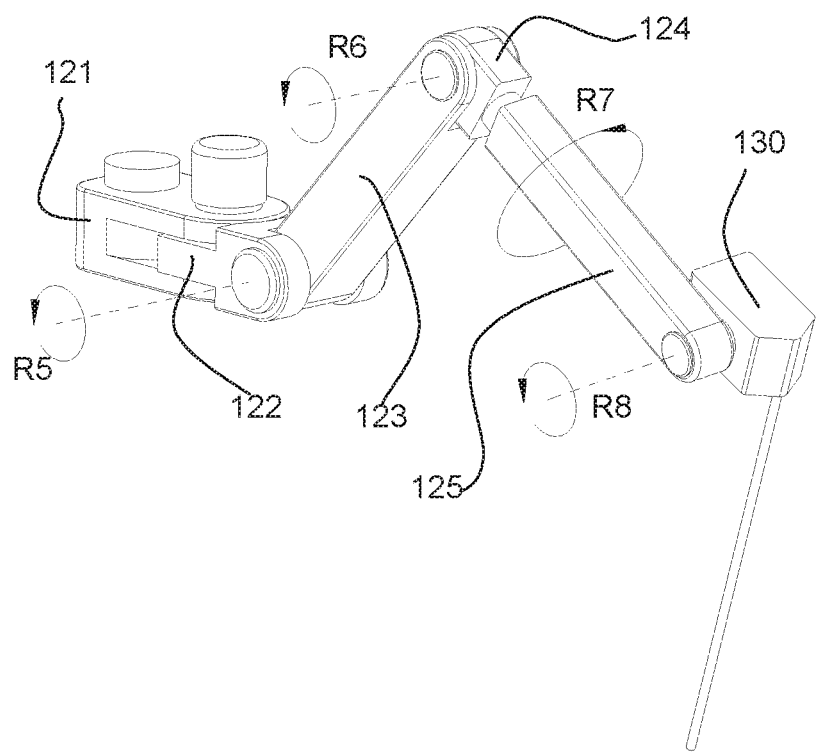
FIG. 4 is a schematic structural diagram of a posture adjustment arm assembly of a surgical robot mechanism with single-port and multi-port minimally invasive surgery functions according to an embodiment of the disclosure.

As illustrated in FIGS. 3 and 4, in the multi-port minimally invasive surgery mode, the base 111, the first cantilever 112, and the second cantilever 113 are located on the same plane, and the function conversion frame 110 presents a plate shape. The surgical tools 130 enter the human body through a wound, respectively, and perform a surgical operation after reaching a lesion location.

Specifically, the posture adjustment arm assembly 120 comprises: a first active arm 121, an active arm joint 122, a second active arm 123, a passive arm joint 124 and a passive arm 125.

A first end of the first active arm 121 is rotatably connected to the function conversion frame 110 (the base 111, the first cantilever 112 or the second cantilever 113). The first active arm 121 is rotatable about a third axis R3, and the third axis R3 is perpendicular to a plane where the first cantilever 112 is located. The first active arm 121 can drive the posture adjustment arm assembly 120 to rotate about the third axis R3.

A first end of the active arm joint 122 is rotatably connected to a second end of the first active arm 121. The active arm joint 122 is rotatable about a fourth axis R4, and the fourth axis R4 is parallel to the third axis R3.

A first end of the second active arm 123 is rotatably connected to a second end of the active arm joint 122. The second active arm 123 is rotatable about a fifth axis R5, and the fifth axis R5 is perpendicular to the fourth axis R4.

A first end of the passive arm joint 124 is connected to a second end of the second active arm 123 by a passive revolute pair. The passive arm joint 124 is rotatable about a sixth axis R6, and the sixth axis R6 is parallel to the fifth axis R5.

A first end of the passive arm 125 is connected to a second end of the passive arm joint 124 by a passive revolute pair. The passive arm 125 is rotatable about a seventh axis R7, and the seventh axis R7 coincides with an extending direction of the passive arm 125. A second end of the passive arm 125 is connected to the surgical tool 130 by a passive revolute pair. The surgical tool 130 is rotatable about an eighth axis R8, and the eighth axis R8 is perpendicular to the seventh axis.

Function, mechanism and quantity of the surgical tool 130 are not limited to a single form. The function conversion frame 110 is provided with a motor operated to drive the first active arm 121 to rotate about the third axis R3. The first active arm 121 is also provided with a motor operated to drive the active arm joint 122 to rotate about the fourth axis R4. The active arm joint 122 is also provided with a motor operated to drive the second active arm 123 to rotate about the fifth axis R5.

Figure 5:
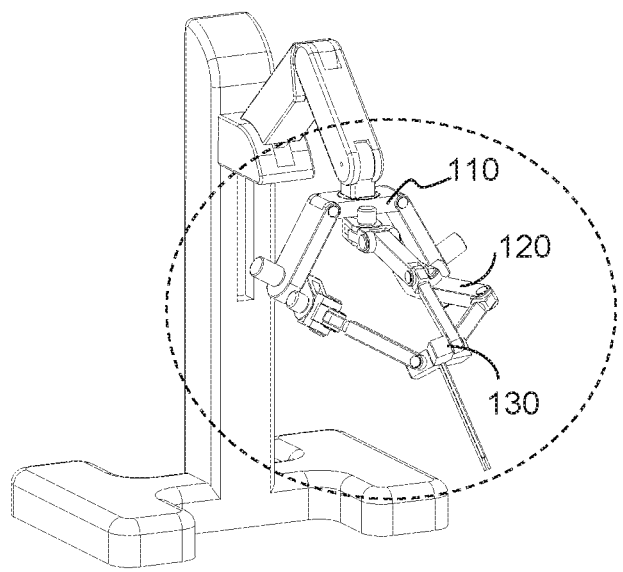
FIG. 5 is a schematic structural diagram of a single-port minimally invasive surgery mode of a surgical robot mechanism with single-port and multi-port minimally invasive surgery functions according to an embodiment of the disclosure.
Figure 6:
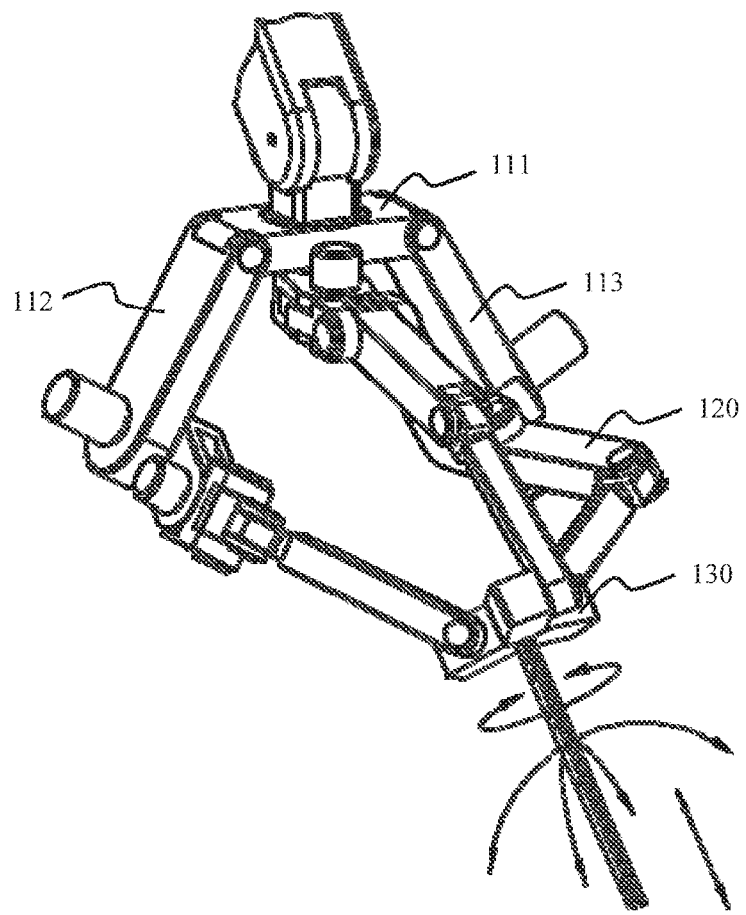
FIG. 6 is a schematic diagram of a partial structure of FIG. 5.
Figure 7:
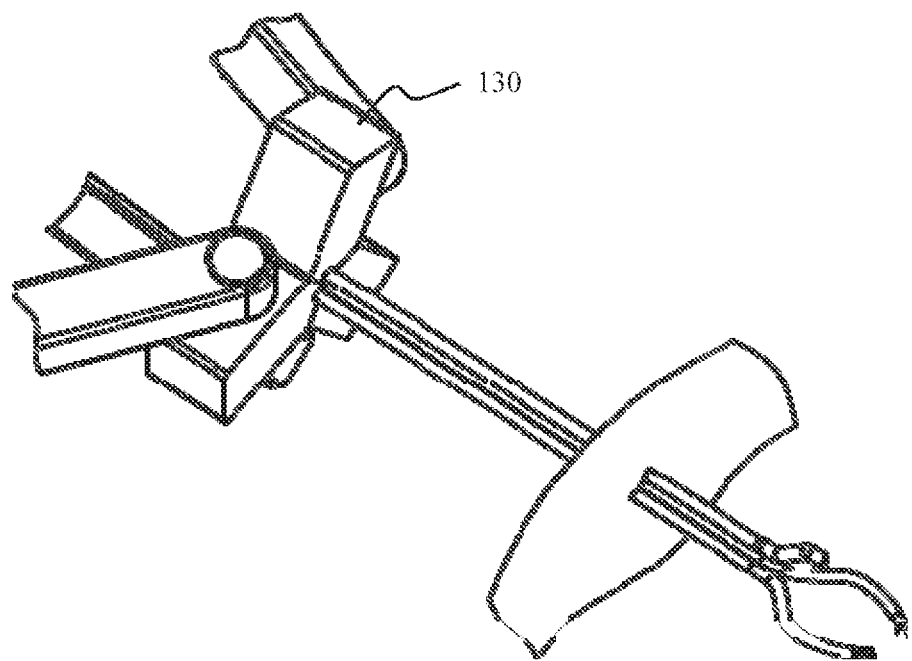
FIG. 7 is a schematic structural diagram of a surgical tool in FIG. 6

In a single-port minimally invasive surgery mode, as illustrated in FIGS. 5 and 6, the first cantilever 112 rotates about the first axis R1, the second cantilever 113 rotates about the second axis R2, and the base 111 forms an angle with each of the first cantilever 112 and the second cantilever 113. The angle is −90°~90°. The plurality of surgical tools 130 are combined together through the plurality of posture adjustment arm assemblies 120, and the combined surgical tools 130 can perform a single-port surgery operation, and can enable an end thereof multi-degree-of-freedom movement in space. In the single-port minimally invasive surgery mode, the combined surgical tools 130 enter the human body through the same wound, and perform the surgical operation after reaching the lesion location. In the multi-port minimally invasive surgery mode, the plurality of surgical tools 130 are separated from each other, and each of the surgical tools 130 enters the human body through a corresponding wound respectively, reaches the lesion location and performs the surgical operation. There is no need to combine the surgical tools 130 to enter the human body through the same wound.

Embodiments are provided according to the following clauses:

1. A surgical robot mechanism with single-port and multi-port minimally invasive surgery functions, comprising:
   a bracket; and
   a slave manipulator connected to the bracket, and supported by the bracket, the slave manipulator comprising:
      a support arm movable along the bracket;
      a function conversion frame fixed on the support arm and operated for the surgical robot mechanism to switch between a single-port minimally invasive surgery mode and a multi-port minimally invasive surgery mode;
      a plurality of posture adjustment arm assemblies connected to the function conversion frame and operated to adjust positions and postures of surgical tools; and
      a plurality of surgical tools connected to the plurality of posture adjustment arm assemblies respectively and operated to perform a surgical operation.

2. The surgical robot mechanism according to clause 1, wherein the function conversion frame comprises:
   a base connected to the bracket;
   a first cantilever rotatably connected to a first end of the base; and
   a second cantilever rotatably connected to a second end of the base,
   the plurality of posture adjustment arm assemblies being connected to the base, the first cantilever and the second cantilever respectively.

3. The surgical robot mechanism according to clause 1, wherein the posture adjustment arm assembly comprises:
   a first active arm with a first end rotatably connected to the function conversion frame;
   an active arm joint with a first end rotatably connected to the first active arm;
   a second active arm with a first end rotatably connected to a second end of the active arm joint;
   a passive arm joint with a first end rotatably connected to a second end of the second active arm;
   a passive arm with a first end rotatably connected to a second end of the passive arm joint, and with a second end rotatably connected to the surgical tool.

4. The surgical robot mechanism according to clause 3, wherein:
   the first active arm is rotatable relative to the function conversion frame about a third axis, the third axis being perpendicular to a surface of the first cantilever;
   the active arm joint is rotatable relative to the first active arm about a fourth axis, the fourth axis being parallel to the third axis;
   the second active arm is rotatable relative to the active arm joint about a fifth axis, the fifth axis being perpendicular to the fourth axis;
   the passive arm joint is rotatable relative to the second active arm about a sixth axis, the sixth axis and the fourth axis;
   the passive arm is rotatable relative to the passive arm joint about a seventh axis, the seventh axis coincides with an extending direction of the passive arm; and
   the surgical tool is rotatable relative to the passive arm about an eighth axis, the eighth axis being perpendicular to the seventh axis.

5. The surgical robot mechanism according to clause 2, wherein in the multi-port minimally invasive surgery mode, the base, the first cantilever and the second cantilever are located on the same plane, and the plurality of surgical tools are separated from each other.

6. The surgical robot mechanism according to clause 2, wherein in the single-port minimally invasive surgery mode, the base forms an angle with each of the first cantilever and the second cantilever, and the plurality of surgical tools are combined together.

7. The surgical robot mechanism according to clause 6, wherein the angle is more than 0 degrees and less than 180 degrees.

So far, embodiments of the present disclosure have been described in detail with reference to the accompanying drawings. It should be noted that in the accompanying drawings or throughout the specification, implementations that are not illustrated or described are all well known to those of ordinary skill in the art and are not described in detail. In addition, definitions of various elements and methods above are not limited to various specific structures, shapes, or ways mentioned in the embodiments, which can be simply changed or replaced by those of ordinary skill in the art.

Finally, it should be noted that the embodiments above are merely provided to illustrate the technical solutions of the present disclosure, not to limit them. Although the present disclosure has been described in detail with reference to foregoing embodiments, those of ordinary skill in the art should understand that the technical solutions described in the foregoing embodiments can still be modified, or some or all of the technical features can be equivalently replaced. In the case of no conflict, the features in the embodiments of the present disclosure can be combined arbitrarily, while such modifications or replacements do not make essence of corresponding technical solutions out of the scope of the technical solutions of the embodiments of the present disclosure.

We claim:

1. A surgical robot mechanism with single-port and multi-port minimally invasive surgery functions, the surgical robot mechanism comprising:
   a bracket; and
   a manipulator connected to the bracket, and supported by the bracket, the manipulator comprising:
      a support arm movable along the bracket;

a function conversion frame fixed on the support arm and configured to enable the surgical robot mechanism to switch between a single-port minimally invasive surgery mode and a multi-port minimally invasive surgery mode;

a plurality of posture adjustment arm assemblies connected to the function conversion frame; and a plurality of surgical tools, each surgical tool connected to a respective posture adjustment arm assembly of the plurality of posture adjustment arm assemblies, each surgical tool configured to enable performance of surgical operation and each posture adjustment arm assembly configured to enable adjustment of a position and posture of a respective surgical tool connected to that posture adjustment arm assembly, wherein at least one of the posture adjustment arm assemblies comprises:

a first active arm with a first end rotatably connected to the function conversion frame, the first active arm rotatable relative to the function conversion frame about a third axis, the third axis being perpendicular to a surface of the function conversion frame;

an active arm joint with a first end rotatably connected to the first active arm, the active arm joint rotatable relative to the first active arm about a fourth axis, the fourth axis being parallel to the third axis;

a second active arm with a first end rotatably connected to a second end of the active arm joint, the second active arm rotatable relative to the active arm joint about a fifth axis, the fifth axis being perpendicular to the fourth axis;

a passive arm joint with a first end rotatably connected to a second end of the second active arm, the passive arm joint rotatable relative to the second active arm about a sixth axis, the sixth axis being parallel to the fifth axis; and a passive arm with a first end rotatably connected to a second end of the passive arm joint, and with a second end rotatably connected to the surgical tool, the passive arm rotatable relative to the passive arm joint about a seventh axis coinciding with an extending direction of the passive arm and the surgical tool rotatable relative to the passive arm about an eighth axis perpendicular to the seventh axis.

2. The surgical robot mechanism according to claim 1, wherein the function conversion frame comprises:

a base;

a first cantilever rotatably connected to a first end of the base; and a second cantilever rotatably connected to a second end of the base, the plurality of posture adjustment arm assemblies being connected to the base, the first cantilever and the second cantilever respectively.

3. The surgical robot mechanism according to claim 2, wherein, in the multi-port minimally invasive surgery mode, the base, the first cantilever and the second cantilever are located on a same plane, and the plurality of surgical tools are separated from each other.

4. The surgical robot mechanism according to claim 2, wherein, in the single-port minimally invasive surgery mode, the base forms an angle with each of the first cantilever and the second cantilever, and the plurality of surgical tools are combined together.

5. The surgical robot mechanism according to claim 4, wherein the angle is more than 0 degrees and less than 180 degrees.

* * * * *